(12) United States Patent
Marriott et al.

(10) Patent No.: US 6,890,901 B2
(45) Date of Patent: *May 10, 2005

(54) HYALURONIC DRUG DELIVERY SYSTEM

(75) Inventors: Christopher Marriott, Lewes (GB); Gary Peter Martin, Lewes (GB); Marc Barry Brown, Watford (GB)

(73) Assignee: Jagotec AG, Hergisweil (CH)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/269,529

(22) PCT Filed: Sep. 29, 1997

(86) PCT No.: PCT/GB97/02665
§ 371 (c)(1),
(2), (4) Date: Jun. 28, 1999

(87) PCT Pub. No.: WO98/13024
PCT Pub. Date: Apr. 2, 1998

(65) Prior Publication Data
US 2001/0005501 A1 Jun. 28, 2001

Related U.S. Application Data

(63) Continuation-in-part of application No. 08/722,909, filed on Sep. 27, 1996, now abandoned.

(51) Int. Cl.[7] .................. A61K 38/00; A61K 51/00; A61K 9/27
(52) U.S. Cl. .................. 514/11; 424/450; 424/1.21
(58) Field of Search .................. 424/1.21, 450, 424/282.1, 85.1, 401, 458; 514/11

(56) References Cited

U.S. PATENT DOCUMENTS

| | | | | |
|---|---|---|---|---|
| 4,517,295 A | * | 5/1985 | Bracke et al. | 435/101 |
| 4,708,861 A | | 11/1987 | Popescu et al. | 424/1.21 |
| 4,861,580 A | * | 8/1989 | Janoff | 424/1.21 |
| 5,244,672 A | | 9/1993 | Huc et al. | 424/450 |
| 5,344,644 A | | 9/1994 | Igari et al. | 424/85.1 |
| 5,401,511 A | * | 3/1995 | Margalit | 424/450 |
| 5,437,867 A | | 8/1995 | Vichroski et al. | 424/401 |
| 5,469,854 A | * | 11/1995 | Unger | 600/458 |
| 5,542,935 A | * | 8/1996 | Unger et al. | 604/190 |
| 5,585,109 A | | 12/1996 | Hayward et al. | 424/450 |
| 5,585,112 A | * | 12/1996 | Unger et al. | 424/450 |
| 5,632,995 A | * | 5/1997 | Wade | 424/282.1 |
| 5,654,000 A | * | 8/1997 | Poli et al. | 424/450 |
| 5,760,023 A | * | 6/1998 | Farrar et al. | 514/150 |
| 6,043,237 A | * | 3/2000 | Meadows et al. | 514/185 |

FOREIGN PATENT DOCUMENTS

| | | |
|---|---|---|
| EP | 446931 A1 | 9/1991 |
| EP | 0 446 931 A1 | 9/1991 |
| EP | 656213 A1 | 6/1995 |
| EP | 697214 A1 | 2/1996 |
| FR | 2 614 787 | 11/1988 |
| FR | 2614787 A1 | 11/1988 |
| FR | 2622104 A1 | 4/1989 |
| GB | 2226002 A | 6/1990 |
| GB | 2 226 002 A | 6/1990 |
| JP | 3-143540 | 6/1991 |
| WO | WO 90/09778 | 9/1990 |
| WO | WO 92/14445 | * 9/1992 |
| WO | WO 92/14446 | 9/1992 |
| WO | WO 92/14448 | 9/1992 |
| WO | WO 93/16732 | 9/1993 |
| WO | WO 96/14083 | 5/1996 |
| WO | WO 97/15330 | 5/1997 |

OTHER PUBLICATIONS

Waldrep et. al.; Cyclosporin A liposome aerosol,(1993) Internat. J. Pharm 97(1–3):205–212, abstract only.*
Yonemitsu et. al.; HVJ –catatonic liposomes: a novel and potentially effective . . . gene transfer to the airway epithelium,(1997) Gene Therapy 4(7):631–638, abstract only.*
Keenan et al (Transplantation 53(1): 20–25, 1992).*
Gilbert et al (Transplantation 56(4): 974–977, 1993).*
Tristani–Firouzi et al (Cutis 61(2 Suppl), 1998).*
Geilen et al (Clin. Exp. Rheumatol. 20(6 Suppl): S871–87, 2002).*
Opthalmed Products, viscoelastic solutions, retrieved from http//www.opthalmed.com/products/page2 on Jan. 15, 2002. See p. 2 of attached print out.*
rxhope.com, record 2246, s0dium hyaluronate, retrieved on Feb. 9, 2001.*
Verma et al. Nature 389: 239–242, especially p. 239, Sep. 1997.*
Anderson et al. Nature 392: 25–30, especially pp. 25 and 30, Apr. 1997.*
N. Weiner et al. "Topical Delivery of Liposomally Encapsulated Interferon Evaluated in a Cutaneous Herpes Guinea Pig Model" (Antimicrob. Agents Chemother., vol. 33, No. 8, pp. 1217–1221 (1989)).

(Continued)

Primary Examiner—Dave T. Nguyen
Assistant Examiner—Richard Schnizer
(74) Attorney, Agent, or Firm—Mintz, Levin, Cohn, Ferris, Glovsky and Popeo, P.C.

(57) ABSTRACT

Pharmaceutical compositions comprising a mixture of hyaluronic acid and liposomes. Preferably, the pharmaceutical compositions further include a pharmaceutically active substance such as cyclosporin A encapsulated in the liposomes. A method for preparing a pharmaceutical composition includes producing liposomes from phospholipids, preferably in the presence of a pharmaceutically active substance (most preferably cyclosporin A) to be encapsulated within the liposomes, and mixing the liposomes with hyaluronic acid. Pharmaceutical compositions of this invention are used, for example, to topically administer pharmaceutical agents effective to treat skin disorders by deposition of that agent in the dermis or sub-dermis while minimizing systemic circulation thereof. These compositions are also administered orally, parenterally and intrarectally.

4 Claims, 12 Drawing Sheets

OTHER PUBLICATIONS

K. Egbaria et al., "Liposomes as a Topical Drug Delivery System" (Advanced Drug Delivery Reviews, 5 (1990) pp. 287–300).

K. Egbaria et al. "Topical Application of Liposomally Entrapped Ciclosporin Evaluated by in vitro Diffusion Studies w/Human Skin[1]" (Skin Pharmacol 1991; 4:21–28).

S. M. Niemiec et al. "The effect of dosing volume on the disposition of cyclosporin A in hairless mouse skin after topical appl of a non–ionic liposomal formulation" (S.T.P. Pharma Sciences 4 (2) 145–149 (1994)).

K. Egbaria et al. "Topical Delivery of Ciclosporin: Evaluation of Various Formulations Using in vitro Diffusion Studies in Hairless Mouse Skin[1]" (Skin Pharmacol 1990; 3:21–28).

L.D. Mayer et al. "Solute Distributions and Trapping Efficiencies Observed in Freeze–Thawed Multilamellar Vesicles" (Biochimica et Biophysica Acta 817, pp. 193–196 (1985)).

J. du Plessis et al. "Topical Delivery of Liposomally Encapsulated Gamma–Interferon" (Antiviral Research 18, pp. 259–265 (1992)).

Ho et al. "Mechanisms of Topical Delivery of Liposomally Entrapped Drugs" Second Int'l Symposium on Recent Advances in Drug Delivery Systems, Feb. 27–28 & Mar. 1, 1985 Salt Lake City, UT USA 61–65 (1985)).

Mezei et al. "Liposomes—A Selective Drug Delivery System for the Topical Route of Administration" (Life Sciences, vol. 26, pp. 1473–1477 (1980)).

Ganesan et al. "Influence of Liposomal Drug Entrapment on Percutaneous Absorption" (International Journal of Pharmaceutics, 20: 139–154 (1984)).

J. du Plessis et al. "The Influence of Particle Size of Liposomes on the Deposition of Drug into Skin" (International Journal of Pharmaceutics, 103: 277–282 (1994)).

Gilhar et al. "Topical Cyclosporine in Psoriasis," American Journal of Dermatology, Correspondence—Letter to the Editor, vol. 18, No. 2, Part 1, pp. 378–379 (1988).

Hermann et al. "Topical Ciclosporin for Psoriasis: In vitro Skin Penetration and Clinical Study" (Skin Pharmacol 1988; 1:246–249).

Rosier et al. "A Rapid Method for Separating Small Vesicles from Suspension" (Analytical Biochemistry 96: 384–390 (1979)).

Laurent et al. "Functions of Hyaluronan" (Journals of the Rheumatic Diseases 1995; 54: 429–432).

Suzuki et al. "The Application of Liposomes to Cosmetics" (Cosmetics & Toiletries, vol. 105 (1990) pp. 65–78).

Mezei "Liposomes as a Skin Drug Delivery System" (Elsevier Science Publishers B.V. (Biomedical Division), pp. 345–358 (1985)).

Syennikova et al. "Farmatsevtychnyi Zhurnal (Kiev)" (Khark Enterp. Prod. Immunobiol. Med. Prep. "BIOLEK", Kharkov, UKR Farmatsevtychnyi Zhurnal (Kiev) pp. 37–40 (1993)) Ukrainian (English Abstract Attached).

Kawaguchi et al. "The Effects of Polysaccharide Chain-–Length in Coating Liposomes with Partial Palmitoyl Hyaluronates" (Carbohydrate Polymers 18 (1992) pp. 139–142).

Margalit "Liposome–Mediated Drug Targeting in Topical and Regional Therapies" (Critical Reviews in Therapeutic Drug Carrier Systems, 12(2&3): pp. 233–261 (1995)).

Haynes et al. "Measurement of an Adhesion Molecule as an Indicator of Inflammatory Disease Activity" (Arthritis and Rheumatism, vol. 34, No. 11 (1991) pp. 1434–1443).

Greaves et al. "Treatment of Diseases of the Eye with Mucoadhesive Delivery Systems" (Advanced Drug Delivery Reviews, 11 (1993) pp. 349–383).

Zignani et al. "Topical Semi–Solid Drug Delivery: Kinetics and Tolerance of Ophthalmic Hydrogels" (Advanced Drug Delivery Reviews 16 (1995) pp. 51–60).

Bourlais et al. "New Ophthalmic Drug Delivery Systems" (Drug Development and Industrial Pharmacy, 21(1), pp. 19–59 (1995)).

Fillit et al. "Immunogenicity of Liposome–Bound Hyaluronate in Mice" (J. Exp. Med. © The Rockefeller University Press, vol. 168 (1988) pp. 971–982).

Thomson, "Immunology of Cyclosporin A—A Review," Aust. J. Exp. Biol. Med. Sci., 61 (Pt. 2) pp. 147–172 (1983).

Williams et al., "Intravenous Cyclosporine and Kidney Function: The Johns Hopkins Experience," Transplantation Proceedings, vol. XVIII, No. 2, Suppl 1), pp. 66–68 (Apr. 1985).

Ellis et al., "Cyclosporine Improves Psoriasis in a Double-blind Study," JAMA, vol. 256, No. 22, pp. 3110–3116 (Dec. 12, 1986).

Griffiths et al., "Total Cyclosporin and Psoriasis," The Lancet, p. 806 (Apr. 4, 1987).

Luke et al., Effects of Cyclosporine on the Isolated Perfused Rat Kidney, Transplantation, vol. 43, No. 6, p. 795 (© 1987).

Mahato et al. "Cationic Lipid–Based Gene Delivery Systems: Pharmaceutical Perspectives", Pharmaceutical Research, vol. 14, No. 7, (1997).

PCT International Search Report (PCT/GB97/02665) mailed Apr. 29, 1998.

Ho et al., "Neoral® in the Treatment of Psoriasis: Consensus Treatment Guidelines," *Journal of Cutaneous Medicine and Surgery,* 1, 4, (1997) (Abstract).

Examination Report from the European Patent Office in counterpart application No. 97943067.5–2114 (Mar. 11, 2003).

\* cited by examiner

Fig. 1a                    Fig. 1b

HYALURONIC DRUG DELIVERY SYSTEM

This is the U.S. National Phase of PCT International Application No. PCT/GB97/02665, International Filing Date 29 Sep. 1997, which is a continuation in part of therefor U.S. patent application Ser. No. 08/722,909, filed 27 Sep. 1996, now abandoned.

BACKGROUND OF THE INVENTION

The present invention relates to pharmaceutical compositions for delivering drugs.

Liposomes and hyaluronic acid have each been used as drug carriers in topical drug delivery systems.

For a review of literature on the use of liposomes as dermal drug delivery vehicles see Gary P. Martin "*Phospholipids as Skin Penetration Enhancers*" King's College University of London, London, United Kingdom, pp. 57–84, 1993.

Liposomes are vesicles in which an aqueous compartment or volume is entirely enclosed by a membrane of lipid molecules which are usually phospholipids. Liposomes may be formed spontaneously when lipids are dispersed in aqueous media, producing a population of liposome vesicles having average maximum diameters ranging from nanometers to microns. Liposomes can be formed such that they will entrap molecules within one or both of the aqueous compartment and the membrane. In fact, liposomes can be formed from natural constituents such that their membrane or membranes forms or form a bi-layer which is similar to the lipid arrangement in natural cell membranes. It is possible that this similarity can be exploited in drug targeting or immune modulation, both in vitro and in vivo, where the liposome's ability to mimic the behavior of natural membranes and, therefore, to be degraded by the same pathways, make liposomes an extremely safe and efficacious drug vehicle for medical use.

Apart from the chemical constituents of liposomes which determine their fluidity, charge density, and permeability, liposomes can be characterized by size and shape. Liposomes have average maximum diameters ranging from 25 nanometers to greater than 1,000 nanometers, which coincide with the average maximum diameters of living cells. As indicated above, liposomes may include a single bi-layer membrane. However, they may also include multiple concentric membrane lamella successively surrounding one another. It is possible, therefore, to group liposomes into one of the following categories based on the number of layers of membranes and relative average diameters: multilamellar vesicle (MLV) liposomes, small unilamellar vesicle (SUV) liposomes, large unilamellar vesicle (LUV) liposomes, and intermediate-sized unilamellar vesicle (IUV) liposomes. See New, R. C, "*Liposomes—A Practical Approach*," Oxford University Press, Oxford, pp. 1–33, 1990.

Several factors such as lamellarity (that is, the number of lamella), lipid composition, charge on the liposomal surface, and the total lipid concentration have been proven to influence drug deposition within the deeper skin strata. See, for example, Weiner et al. "*Topical Delivery of Liposomally Encapsulated Interferon in a Herpes Guinea Pig Model*," Antimicrob. Agents Chemother., 33: 1217–1221, 1989. There has also been much discussion on the mechanism of liposome diffusion in skin. Originally, it was thought that liposomes diffused intact through to the dermis where they became localized as set forth in Mezei, M. and Gulasekharam, V., "*Liposomes—A Selective Drug Delivery System for the Topical Route of Administration*," Life Sci., 26: 1473–1477, 1980. Later, this theory was criticized by Ganesan et al. "*Influence of Liposomal Drug Entrapment on Percutaneous Absorption*," Int. J. Pharm., 20: 139–154, 1984; and Ho et al. "*Mechanism of Topical Delivery of Liposomally Entrapped Drugs*," J. Controlled Rel., 2: 61–65, 1985, as it was thought that the densely packed stratum corneum would not allow the passage of liposomes through to the epidermis and dermis. Egbaria, K. and Weiner, N., "*Topical Application of Liposomal Preparations*," Cosmet. Toilet., 106: 79–93, 1991, postulated that molecular mixing of the bi-layers of the liposome and the stratum corneum takes place. There have also been indications that the follicular pathway contributes to the liposomal delivery of drugs into the skin as discussed in Du Plessis et al. "*Topical Delivery of Liposomally Encapsulated Gamma-Interferon*," Antiviral Res., 18: 259–265, 1992; and evidence that the size of the liposome is important as described in Du Plessis et al. "*The Influence of Particle Size of Liposomes on the Deposition of Drug into Skin*," 103: 277–282, 1994.

Liposomes have been used also for non-topical or parenteral drug delivery. For evaluation of the effectiveness of liposomal drug delivery, researchers have determined (1) the effect of components of biological fluids on the structural integrity of liposomes and (2) the rates at which liposomes are cleared from the administration site and distributed into the tissues. With both parameters, the behavior of liposomes is dictated by their structural attributes. Specifically, as the stability of the liposomes increases their rate of clearance from the site of administration decreases. Their circulation times, however, can be controlled by using smaller liposomes, altering their lipid composition or rendering the liposomes hydrophilic. Gregoriadis, G., "Liposomes in Drug Delivery: Present and Future," 346–352.

Notwithstanding this extensive knowledge and literature, liposomes alone are sometimes deficient as drug delivery vehicles due to their instability and/or their unsatisfactory penetration characteristics in particular systems.

As discussed and claimed in PCT Publication No. 93/16732, hyaluronic acid has also been known as a vehicle for topical delivery of pharmaceutical agents. Hyaluronic acid is extremely hydrophilic, however, and thus, has not been successfully combined with hydrophobic drugs such as cyclosporin A.

It has been discovered that there are many proteins which bind HA, including several different cell receptors having a variety of functions, including receptors related to tumor cells. Thus, it has been suggested that based on the variety of modes by which HA can interact with cells it must have several regulatory functions.

Many drugs, one example of which is cyclosporin A (molecular formula $C_{62}H_{111}N_{11}O_{62}$; sometimes referred to hereafter as CsA), are difficult to administer. Cyclosporin A is a cyclic undecapeptide antibiotic produced by the fungus *Tolypocladium Inflatum* and is highly lipophilic. Cyclosporin A is also virtually insoluble in water and hydrophobic, as indicated above. Cyclosporin A is a potent T-lymphocyte cell-specific immunosuppressant which is primarily used for prophylaxis and treatment of organ rejection in renal, hepatic, cardiac, and pancreatic transplantation. It has also been administered orally or intramuscularly in the treatment of psoriasis as discussed in Ellis et al. "*Cyclosporin Improves Psoriasis in a Double Blind Study*," JAMA, 256:3110–3116; Griffiths et al. (1987) "*Cyclosporine and Psoriasis*," Lancet, i: 806, 1986.

When administered orally, cyclosporin A is usually administered as an olive oil based micro emulsion solution mixed with beverages. Cyclosporin A may also be administered as an intravenous injection. The drug is solubilized using the solubilizing agent Chremophor EL, a mixture of olive oil and polyethoxylated castor oil (also known by the tradename Neoral). Systemic administration of such a cyclosporin A formulation, however, leads to several side effects such as anaphylactic reactions, adult respiratory distress syndrome, nephrotoxicity, gastrointestinal problems, hepatoxicity, angioedema, and mild tremor as reported in Thomson, A. W., "*Immunobiology of Cyclosporin: A Review*," Aust. J. Exp. Biol. Med. Sci., 61: 147–172, 1983. It is believed that a number of these adverse reactions are caused by the drug vehicle itself as discussed in Williams et al. "*Intravenous Cyclosporin and Kidney Function: The Johns Hopkins Experience*," Transplant. Proc., 18: 66–73, 1986; and Luke et al. "*Effects of Cyclosporin on the Isolated Perfused Rat Kidney*," Transplantation, 43: 795–799, 1987.

The incidence of systemic side effects may be markedly reduced by delivering cyclosporin A topically, although previous studies involving transdermal delivery of cyclosporin A for the treatment of psoriasis using oil in water emulsions have proven this delivery method to be ineffective. See, for example, Gilhar et al. "*Topical Cyclosporin in Psoriasis*," J. Am. Acad. Dermatol., 18: 378–379, 1988; and Hermann et al. "*Topical Cyclosporin for Psoriasis*," Skin Pharmacol., 1: 246–249, 1988. In addition, the side effects may be reduced by using a less antagonistic carrier. Thus, there is a need for a non-toxic dosage form of cyclosporin A and a safe route of administration.

A combination of CsA and liposomes is not satisfactory because of the physical instability of the combination. That is, liposomes in the liposome/CsA combination may break down causing the CsA to separate from the liposomes or the CsA may separate from the liposomes even where the liposomes do not break down. A suitable combination had yet to be developed. Hyaluronic acid, alone, also fails as a carrier for CsA because of the lipophilic, hydrophobic nature of CsA.

HA and liposomes, individually, fail also to be good carriers for other drugs which are lipophilic and hydrophobic.

SUMMARY OF INVENTION

In its most general form, the present invention comprises a mixture of liposomes and hyaluronic acid (HA). The stability of essentially any liposome is enhanced by such admixture and the dermal penetrability and drug targeting ability of the mixture typically exceed those of either component alone.

For these reasons, the admixture comprises an excellent carrier for topically and non-topically applied pharmaceuticals. The present invention, therefore, also includes combinations of such mixtures with pharmaceutical agents having activity in the dermis or sub-dermis and pharmaceutical agents which are generally administered orally, parenterally or intrarectally.

The present invention is particularly efficacious for dermal therapeutic compositions in which the active pharmaceutical agent is incompatible with an otherwise desirable delivery vehicle. One such pharmaceutical agent is cyclosporin A (hereafter sometimes CsA).

The encapsulation of cyclosporin A within liposomes to form a liposome/cyclosporin A composition, enables cyclosporin A to be combined with hyaluronic acid (sometimes referred to hereafter as HA) to form an efficacious pharmaceutical composition which is the preferred embodiment of the present invention.

A topical pharmaceutical composition, comprised of HA in combination with liposomes containing CsA, is a preferred embodiment of the present invention, as is a therapeutic method for treating an animal by topically administering to an internal or external body part a therapeutically effective amount of such a pharmaceutical composition. Still another aspect of the present invention is a method of manufacturing such a composition by producing liposomes from phospholipids, and mixing the liposomes with hyaluronic acid. The method further includes encapsulating a pharmaceutically active substance such as cyclosporin A in the liposomes during liposome production.

Another aspect of the invention is a pharmaceutical composition of HA and liposomes containing CsA or other active ingredients administered orally, parenterally or intrarectally and methods for treating an animal by orally, parenterally or intrarectally administering an effective amount of such a pharmaceutical composition.

The pharmaceutical compositions according to the invention may also advantageously be used in so-called "gene-therapy" to introduce a selected polynucleotide (e.g. a DNA or RNA), to a target somatic cell.

The compositions of the invention are most advantageously adapted for use in gene therapy by arranging for the selected polynucleotide (preferably in the form of a plasmid or vector) to be located within the liposomes.

The invention further provides according to a further aspect, the use of hyaluronic acid in the manufacture of a pharmaceutical composition for use in gene therapy. In such a use, the pharmaceutical composition may, as indicated, include liposomes, but the use of hyaluronic acid in gene therapy independently from the use of liposomes is also encompassed.

The selected polynucleotide may, for example, comprise sequences encoding genetic information which is absent from the target gene, or is present, but in defective or mutated form. Thus, for example in certain disease states having a genetic basis, such as cystic fibrosis, a gene responsible for a normal physiological function may be defective. Another example is treatment of Gaucher's disease using a DNA sequence coding for glucocerebrosidase. Using gene therapy, the absence of a fully functional gene may be at least partially rectified by administering a therapeutic agent comprising a selected polynucleotide which includes sequences associated with the sequence of the fully functional gene. These sequences may then interact with the target somatic cells, for example by becoming integrated into the nucleic acid thereof, so that the somatic cells are transformed to an essentially normal state.

Other examples include polynucleotides associated with cancer suppressor genes such as, for example, the p53 cancer suppressor gene.

The selected polynucleotides for use in gene therapy may advantageously be administered in a form that promotes interaction with a specific target tissue. Thus, for example, in the treatment of cystic fibrosis it is advantageous for the composition to be administered in a form that is suitable for administration to the lungs, e.g. a solution or suspension suitable for infusion into the lungs. Similarly for treatment of localised malignancies, it is advantageous for the compositions according to the invention to be provided in a form which promotes retention at the site of desired action. For example in the case of treatment of retinoblastoma by a gene therapy that involves use of cancer suppressor gene sequences, the compositions according to the invention may advantageously be in the form of an ocular implant.

The polynucleotides used in gene therapy may advantageously include sequences which are adapted to promote integration into the nucleic acid of the target cells, for example sequences which are homologous with sequences of target genes, so that integration can occur as a result of homologous recombination. Other systems involve incorporating the selected polynucleotide into a plasmid or vector which is capable of transfecting the target cells. Examples include adenovirus vector systems, in particular adenoviruses which are disabled so that undesirable characteristics of the native adenovirus vectors are eliminated. In particular the adenoviruses are preferably disabled so that reproduction thereof is inhibited or suppressed.

Plasmid-based expression systems containing a selected polynucleotide as described may include DNA sequences which are adapted to control the in vivo expression of the selected polynucleotide. Thus, for example, a promoter/enhancer region may be included, such as the cytomegalovirus immediate-early gene promoter/enhancer and transcription stabilizers that promote the stability of transcribed mRNA. For further details of such control mechanisms, see "Cationic Lipid-Based Gene Delivery Systems: Pharmaceutical Perspectives", Mahato, R. I. et al. Pharmaceutical research, 14, No. 7 (1998), pp.853–859 and the references cited therein.

Other examples of polynucleotides which can be used in gene therapy include so-called "anti-sense" polynucleotides, which are adapted to interact with nucleic acid associated with cells in a disease state in order to inhibit duplication, transcription and/or expression of gene products associated with the disease state. Thus, for example, anti-sense polynucleotides may be designed to interact with viral DNA or RNA and thus inhibit viral replication. Alternatively, anti-sense polynucleotides may be designed to interact with mutated genes associated with disease states such as cancer.

Selecting an appropriate carrier for the selected polynucleotides used in gene therapy is important, because the selected polynucleotide may often be a relatively large molecule (1000–5000 kDA) which may be susceptible to degradation. Furthermore, it is frequently important for the selected polynucleotide to be directed to a specific cell compartment, e.g. the nucleus. Currently available pharmaceutically acceptable excipients often lacking in providing the desired characteristics of targeting the selected polynucleotide to the nucleus and protecting the selected polynucleotide from degradation.

The use of a combination of hyaluronic acid and liposomes, in accordance with the invention may advantageously used to overcome difficulties associated with methods of gene therapy devised hitherto. In such use, the selected polynucleotide (which may comprise any of the examples referred to above and which advantageously comprises a plasmid or viral vector), can be located in the lumen of the liposome, where it is protected from agents such as cellular nucleosidases which might cause degradation thereof. As indicated, the presence of hyaluronic acid, in combination with liposomes, results in enhanced stability and penetration characteristics compared to liposomes alone.

DETAILED DESCRIPTION OF THE INVENTION

Figure 1:
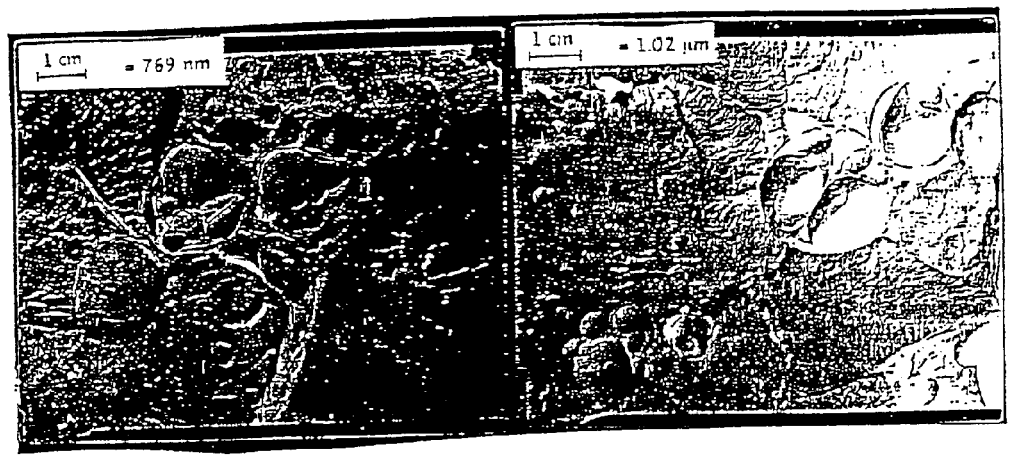
FIG. 1A is a Freeze Fracture photographic image showing negatively charged liposomes at 13,000× magnification.
FIG. 1B is a Freeze Fracture photographic image showing negatively charged liposomes at 9,800× magnification.

As generally used herein, HA refers to a hyaluronic acid compound that upon dissolution yields hyaluronic acid. The efficacious pharmaceutical compositions of the invention comprise a mixture of liposomes with a sufficient amount of HA to function as an effective drug carrier for the liposomes (and any drug contained therein), with which the HA is mixed. The amount of HA required for that purpose is dependent on the molecular weight fraction of HA. For example, where the molecular weight is relatively low, the concentration may be relatively high, and vice versa. HA may have an average molecular weight in the range of 10,000 to 1,000,000 daltons, preferably the largest fraction being 400,000 to 800,000 daltons. Hyaluronic acid is usually provided in the form of aqueous solutions of HA salts, such as sodium or potassium hyaluronate, with an HA concentration in the range of 0.3 to 2.5% by weight. Compositions having HA within these ranges of concentrations and average molecular weights will generally be effective as a topical or non-topical drug carriers for a wide range of liposomes.

As discussed below, liposomes are generally prepared using two techniques, a Freeze Thaw Cycle technique and a Conventional Film technique. Both techniques produce predominantly multilamellar vesicle (MLV) liposomes (MLV's typically include five or more concentric lamellae and have average maximum diameters in the range of 100 to 1,000 nanometers). Other techniques of liposome preparation may also be used. Regardless of the method by which such liposomes are prepared, they may be rendered more stable and more useful by combination, in a simple mixture, with HA.

Moreover, liposomes do not appear to disrupt the viscoelastic nature of HA. Indeed, the strength of the HA gel is apparently increased. One possible explanation is that liposomes promote hydrophobic bonding. It is also possible that HA helps to stabilize and protect the liposomes from breakdown, thus overcoming a typical problem associated with liposome delivery.

It has been shown that it is possible to form a gelatinous pharmaceutical composition including cyclosporin A and hyaluronic acid using liposomes. By mixing HA with a liposome/cyclosporin A composition to form a mixture thereof, cyclosporin A can be effectively targeted to and deposited in the epidermis, dermis, and sub-dermis and junctions therebetween, with minimal systemic delivery.

Furthermore, the HA-liposome composition containing cyclosporin A or other active ingredients can target particular sites in the body when delivered orally, parenterally or intrarectally. This is attributed to the targeting ability of both components. Specifically, HA's interactions with different cell receptors make it a suitable candidate for a drug targeting carrier for non-topical administration of a drug.

The present invention also is directed to a method for treating a condition susceptible of treatment by a pharmaceutical agent which may be disposed in a dermal region by topical application of the agent on the surface of the dermal region in a carrier composition comprising a mixture of liposomes and HA. Those skilled in the art may readily determine the relative amounts of agent, liposome, and HA best suited in a given case, but in any case, the HA carrier must be in sufficient concentration to cause substantial delivery of a non-toxic and therapeutically effective amount of the pharmaceutical agent to a region of the dermis susceptible of treatment. For guidance, one may refer, for example, to Patent Cooperation Treaty Publication No. WO 93/16732 (Falk et al.; published Sep. 2, 1993) which describes dosage levels of combinations of HA and medicinal or therapeutic agents in detail.

Originally, it was thought that liposomes may function as penetration enhancers. That is, it was thought that liposomes may facilitate tissue penetration to allow delivery of a drug. However, it is now believed that liposomes may have a similar mechanism to that proposed for hyaluronic acid. That is, liposomes may enhance the localized delivery of drug within the epidermis and/or dermis and, thereby, reduce the amount of a drug released to systemic circulation. Such an effect is of an obvious advantage if the desired delivery site lies within the skin layers. Also, localized delivery may be beneficial for drugs that must be applied over a prolonged period of time, over extensive areas of the body, or where systemic toxicity may be a problem. Such localized delivery of xenobiotic or other pharmaceutical agents would be desirable, for example, for the topical use of corticosteroids; cytotoxic agents; anesthetics; retinoids; sex hormones; antifungal, antibacterial and antiviral agents for treatment of a variety of skin disorders; immunosuppressants, and antiproliferatives.

To show that essentially any liposome could be combined with HA without reducing the effectiveness of the HA as a carrier and delivery vehicle, the effect of negatively charged, positively charged, and neutral liposomes on the viscoelastic properties of a HA gel were studied in the absence of any drug. The viscoelastic properties were studied by observing the storage modulus (G') and loss modulus (G") of the liposomes and HA gel composition where the HA is 2.5% by weight of the composition at various frequencies and at constant strain or displacement. Storage modulus (G') is an indicator of the elasticity of a substance and, therefore, is an indication of the strength of the HA gel composition and a gauge of the stability of the three dimensional structure of the gel. Stability of the three dimensional structure refers to the ability of the HA gel composition to maintain a three-dimensional form. The higher the value of G' at a given frequency the more elastic the HA gel composition and, therefore, the greater strength the HA gel composition possesses. Loss modulus (G") is an indicator of the viscosity of a substance. The higher the value of G" at a given frequency, the more viscous the HA gel composition.

The frequency at which the storage modulus (G') crosses the loss modulus (G") is known as the cross-over frequency. Because the loss modulus (G") is an indicator of the viscosity of a substance and the storage modulus (G') is an indicator of the elasticity of a substance, the cross-over frequency provides a way of determining the viscoelastic properties of a substance. For example, if the substance being studied is a gel, the lower the cross-over frequency, the more viscoelastic the gel. A viscoelastic material is a viscous material that also exhibits certain elastic properties such as the ability to store energy of deformation. In the context of gels, the more viscoelastic a gel, the more stable the gel.

The stability of liposome formulations has been determined by studying the rheological profiles of various liposome/HA gel compositions and comparing these profiles at time equals zero and after seventy-two (72) hours. The tests were continued beyond the 72 hour period and results appeared consistent for 7 days. Other tests have indicated comparable stability for up to 30 days.

The characteristics of compositions of the present invention are demonstrated in the following tests, procedures, and results.

Materials

Phosphatidyl choline (lecithin; Grade 1, having a purity greater than 99%) and phosphatidyl serine and glycerol (having a purity greater than 99%) were obtained from Lipid Products (Redhill, Surrey, UK.). Cholesterol, 0.05 molar HEPES buffer (a zwitterionic buffer) having a pH of 7.4, and stearylamine (98% gas chromatography) were purchased from the Sigma Chemical Co. (Poole, Dorset, UK.). All solvents were high performance liquid chromatography (HPLC) grade and were supplied by Fisher Scientific (Loughborough, Leics, UK.). Sodium hyaluronic acid (product Nos. HG4003 and HG4001) having average molecular weights in the range of 10,000 to 1,000,000 daltons was supplied by Hyal Pharmaceutical Corporation. United States pharmaceutical grade cyclosporin A was obtained from Atlantic Chemical Co., (Ontario, Canada).

Liposome Production, Drug Loading Techniques, and Addition of HA

Two techniques for producing liposomes were used. Both techniques produced MLV liposomes which allowed incorporation of the maximum amount of a drug into the liposomes. The two techniques carried out were a Freeze Thaw Cycle technique devised by Mayer et al. "*Solute Distributions and Trapping Efficiencies Observed in Freeze-Thawed Multilameller Vesicles*," Biochim. Biophys. Acta, 817: 193–196, 1985, and the much simpler Conventional Film technique described by New "*Liposomes—A Practical Approach*," Oxford University Press, Oxford, pp. 1–33, 1990. The Conventional Film technique has fewer production steps than the Freeze Thaw Cycle technique.

In both techniques, cyclosporin A was entrapped within liposomes at the point of liposome production Using the Conventional Film technique, cyclosporin A was first added to lipids comprising phosphatidyl choline (PC), cholesterol (C), and bovine phosphotidyl serine (PS) or phosphotidyl glycerol (PG) in a molar ratio of 1.0 PC: 0.5 C: 0.1 PG or PS. Other lipids and molar ratios may also be used. The lipids and cyclosporin A were then dissolved in a 2 to 1 ratio of chloroform and methanol in a round bottom flask. The solvents were then removed by rotary evaporation under a stream of nitrogen gas, followed by drying the lipid and cyclosporin A combination under vacuum overnight to form a lipid and CsA film. The lipid and CsA film was then hydrated with HEPES buffer (0.05 M, pH 7.4) thereby forming liposomes and having CsA encapsulated therein. The CsA/liposomes composition comprised 10% by weight phosphotidyl choline, 2.5% by weight cholesterol, 1.0% by weight phosphotidyl serine or glycerol, and 1.35% by weight CsA. Pure, dry sodium hyaluronic acid powder (product No. HG4003) was then added to the CsA/liposome combination such that the concentration of HA was 2.5% by weight. The addition of HA to the CsA/liposome combination reduced the final concentrations of the liposomes to 13.165% (9.75% by weight phosphotidyl choline, 2.44% by weight cholesterol, 0.975% by weight phosphotidyl serine or glycerol) and CsA to 1.32% by weight of the composition.

For example, a film comprising 1.0 gram phosphotidyl choline, 0.25 grams cholesterol, 0.10 grams phosphotidyl serine or glycerol, and 0.135 grams CsA was hydrated with 8.515 grams HEPES buffer to obtain 10 grams of liposomes having 0.135 grams CsA encapsulated therein, or 13.5 milligrams CsA per gram liposomes. Pure, dry sodium hyaluronic acid powder was then added to and hydrated with the CsA/liposome combination to provide a final HA concentration of 2.5% by weight. Before the HEPES buffer was used, the HEPES buffer was filtered and degassed to remove oxygen, and to minimize oxidation and the degradation of the unsaturated lipids.

Cyclosporin Assay

The amount of cyclosporin A encapsulated in liposomes was analyzed using high performance liquid chromatography (HPLC) with a 15 centimeter C18 Hichrom column with a 5 centimeter guard (obtained from Reading, Berks, UK.). The flow rate was 1.5 milliliters per minute and the column temperature was 50° C. The mobile phase was a mixture of 75% by weight acetonitrile and 25% by weight water, and the eluant was monitored at 207 nanometers using fluoranthene as a temporary internal standard.

Rheology Studies

The rheological profiles of the liposome/HA gel composition according to the present invention were studied using a CarriMed UK CSL Rheometer (TA Instruments, Leatherhead, Surrey, UK.). The rheometer was fitted with a 4 centimeter diameter acrylic parallel plate and all tests was carried out at 25° C. without a solvent trap. The rheological profiles studied were the storage modulus (G'; an indicator of the elasticity of the gels) and the loss modulus (G"; an indicator of the viscosity of the gels) versus frequency at constant strain or displacement.

Freeze Fracture

Freeze Fracture photographic images for liposome/HA gel compositions according to the present invention were obtained. The Freeze Fracture images were obtained by placing the liposome/HA gel composition between two copper plates; and then cryofixing, breaking, and etching the gel under high vacuum and low temperature. Liposome/HA gel composition samples according to the present invention were then vapor coated with platinum (Pt) and carbon (C) to form replicas. By "replica" is meant a negative photographic image of the liposomes/HA gel composition. After cleansing, the replicas were then assessed on a Philips EM301G mode Transmission Electron Microscopy unit (from Eindhoven, Netherlands).

Particle Sizing

Most commercial particle sizing techniques use photon correlation spectroscopy (PCS). PCS uses the time dependence of intensity fluctuations in scattered laser light, which is due to the Brownian motion of particles in solution/suspension, to measure particle size. Because small particles in solution diffuse more rapidly than large particles, the rate of fluctuation of scattered light varies accordingly. Analysis of the intensity fluctuations allows one to determine the diffusion coefficient (D), and using the Stokes-Einstein equation (1), the equivalent hydrodynamic radius of particles ($R_h$) may be calculated for particles ranging from 3 nanometers to 3 micrometers. The Stokes-Einstein equation defines the diffusion coefficient as:

$$D = kT/6\pi\eta R_h \tag{1}$$

where k is the Boltzmann's constant, T is the absolute temperature, and n is the solvent viscosity. The average maximum diameters of the liposome/HA gel compositions according to the present invention were determined using a Malvern Autosizer Model 700 (from Malvern, Worcs., UK.). A 1/200 dilution of the liposome suspension was dispensed into a clean cuvette and monitored at a thermostatically controlled temperature of 25° C.

Experimental Results and Discussion

The types of liposome vesicles used to form the liposome/HA gel compositions according to the present invention were determined using the Freeze Fracture technique.

FIGS. 1A and 1B, prepared using the Freeze Fracture technique, are photographic images of negatively charged liposomes (prepared using a Freeze Thaw Cycle technique) at 13,000× and 9,800× magnification, respectively. The Freeze Fracture images show that predominantly multilamellar vesicle (MLV) liposomes were formed. When determining the type of liposome vesicles present, care must be taken using the Freeze Fracture technique because the probability of fracture is greater for large vesicles than for small vesicles. This often results in misidentification of the fracture courses in one membrane and causes MLV liposomes to be mistaken for large unilamellar vesicle (LUV) liposomes.

Figure 2:
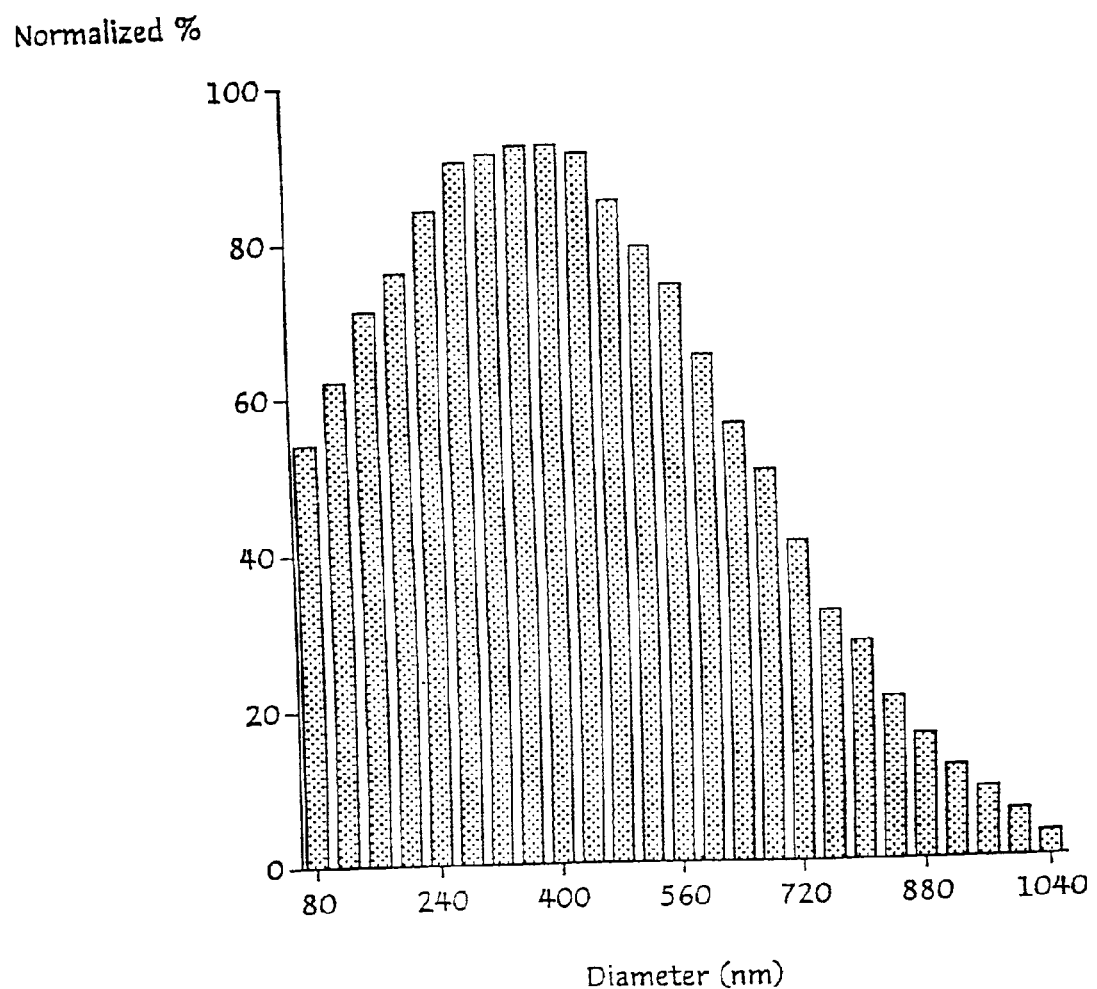
FIG. 2 is a graph showing particle size distribution of negatively charged liposomes in HEPES buffer having a pH of 7.4 and 0.1 M.

FIG. 2 is a graph showing the average maximum diameter distribution for negatively charged liposomes (as shown in, and described with respect to FIGS. 1A and 1B) in HEPES buffer at 0.05 M and having a pH of 7.4. Average maximum liposome diameters were in a range of 80 to 1040 nanometers, with a majority in the range of about 200–900 nanometers. Such liposomes permit the maximum amount of cyclosporin A to be encapsulated within the liposomes. The liposomes were then mixed with hyaluronic acid (product No. HG4001; average molecular weight 630,000 daltons); and the flow properties examined to determine the effect that the liposomes had on the viscoelastic properties of HA.

Figure 3:
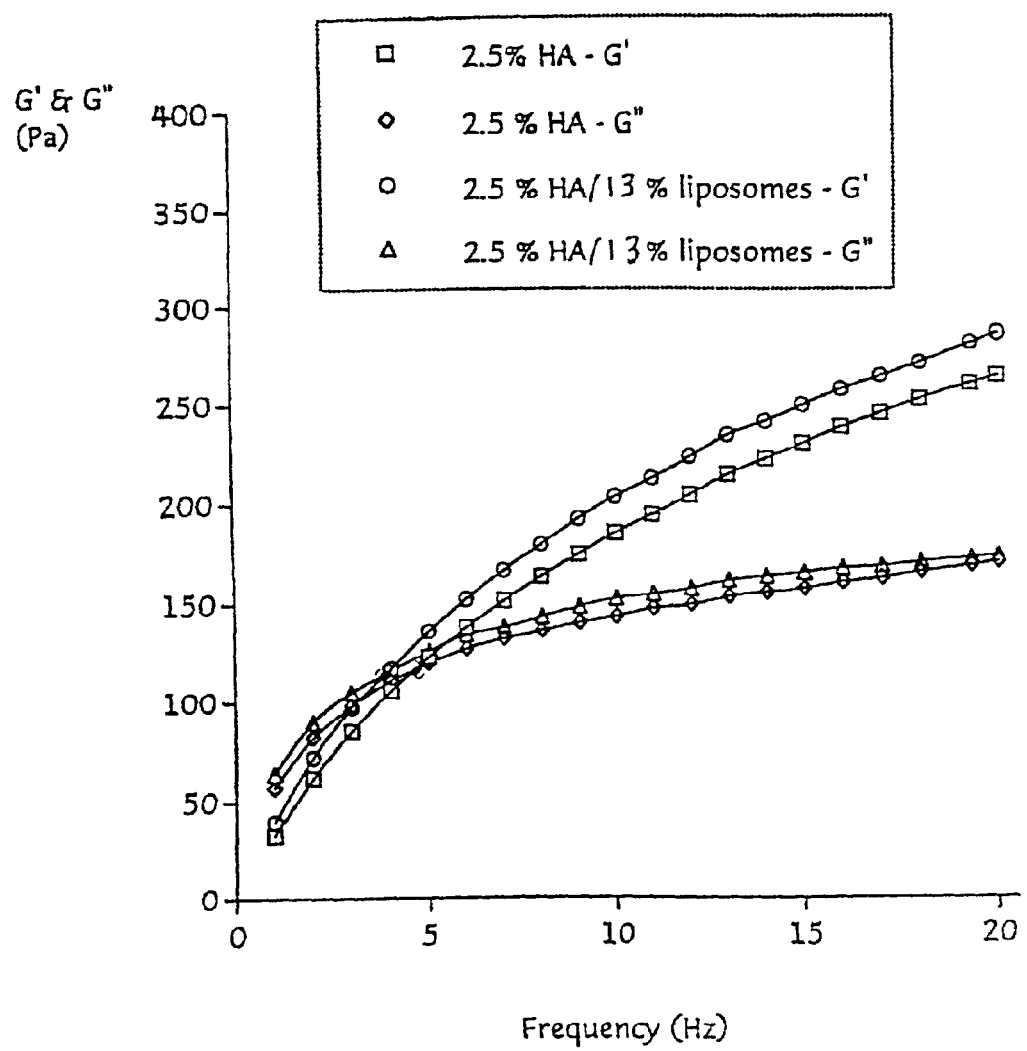
FIG. 3 is a graph showing an indicator of elasticity as measured by the storage modulus (G') and an indicator of viscosity as measured by the loss modulus (G") for hyaluronic acid, with and without negatively charged liposomes versus frequency.

FIG. 3 is a graph showing the storage modulus (G') and the loss modulus (G") for sodium hyaluronate (product No. HG4001; average molecular weight 630,000 daltons), with and without negatively charged liposomes (as shown in, and described with respect to FIGS. 1A and 1B), versus frequency. At about 13% by weight liposomes and 2.5% by weight HA, there is no disruption in the HA gel structure. Indeed, the storage modulus (G'; open circle) and the loss modulus (G"; open triangle) for the combination of HA and negatively charged liposomes were slightly higher than the G' (open square) and G" (open diamond) for the HA gel composition alone. Note that the higher the G', the more elastic the gel; and the higher the G", the more viscous the gel. Also, the lower the frequency at which G' and G" cross each other, the more viscoelastic the substance. The frequency at which G' and G" cross each other for the HA/liposome composition is about 4 hertz, while the frequency at which G' and G" cross each other for HA alone is about 5 hertz indicating that the HA/liposome compositions are slightly more viscoelastic than HA alone. This increased viscoelasticity indicates that a stable HA/liposome formulation can be achieved.

As discussed above, cyclosporin A was also encapsulated within negatively charged liposomes using a Conventional Film technique. Using a Conventional Film technique, negatively charged liposomes (as shown in, and described with respect to FIG. 1) were loaded with cyclosporin A at 13.5 milligrams per gram of liposome. The encapsulation of cyclosporin A within the liposomes was determined using protamine aggregation and centrifugation followed by disruption of the vesicles with Triton X100, as discussed in Rosier et al. "*A Rapid Method for Separating Small Vesicles from Suspension*," Anal. Biochem. 96: 384–390, 1979, followed by HPLC analysis. The liposome/cyclosporin A composition was then combined in mixture with HA.

Figure 4:
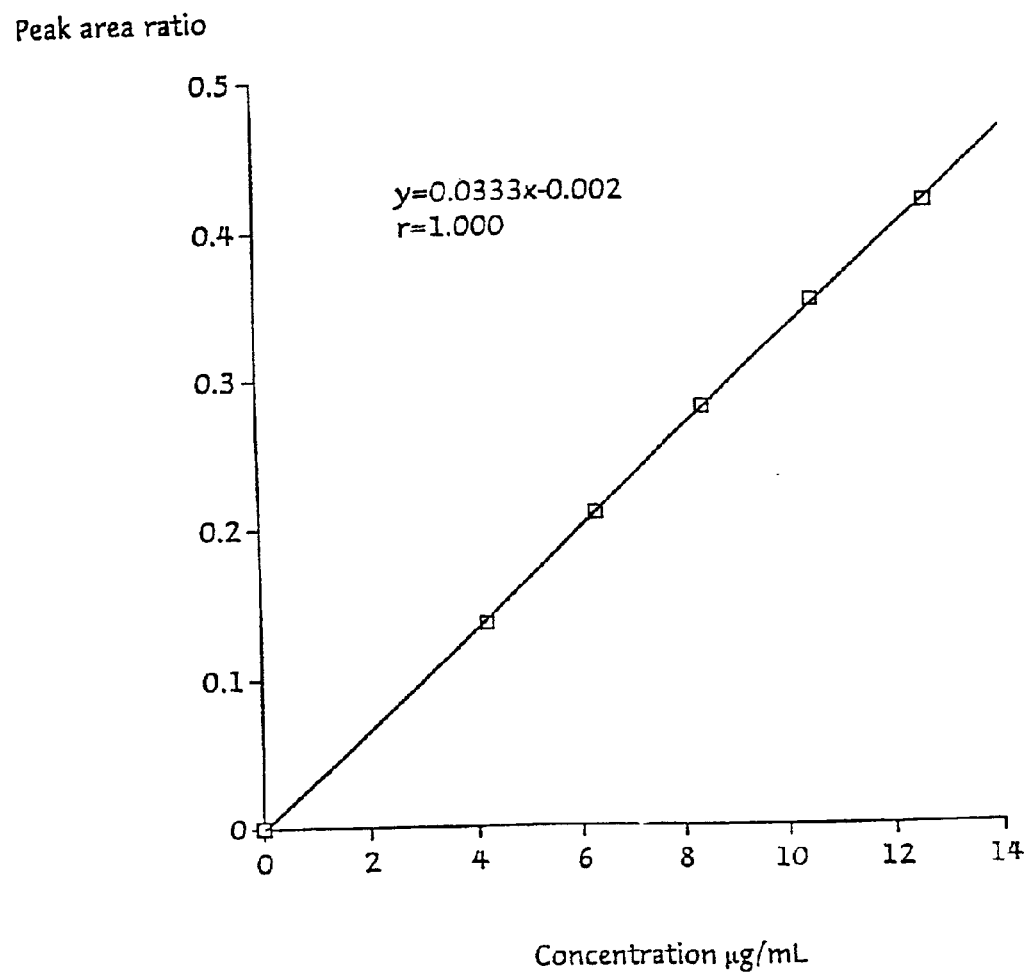
FIG. 4 is a curve showing the peak area ratio versus concentration using fluoranthene as a temporary internal standard, which curve was used to calibrate the high performance liquid chromatography (HPLC) unit used to determine the amount of cyclosporin A encapsulated in liposomes.

FIG. 4 is a calibration curve showing the peak area ratio versus concentration using fluoranthene as a temporary internal standard. This calibration curve was used to calibrate the high performance liquid chromatography (HPLC) equipment prior to analysis of the HA/liposome/cyclosporin A composition to determine the amount of cyclosporin A encapsulated within the liposomes. The assay indicated that all of the cyclosporin A was encapsulated within the liposomes in HA. This finding was further supported by negative staining electron microscopy observations which showed that no free cyclosporin A particles were present in crystalline form after cyclosporin A was encapsulated within the liposomes.

Figures 5A, 5B:
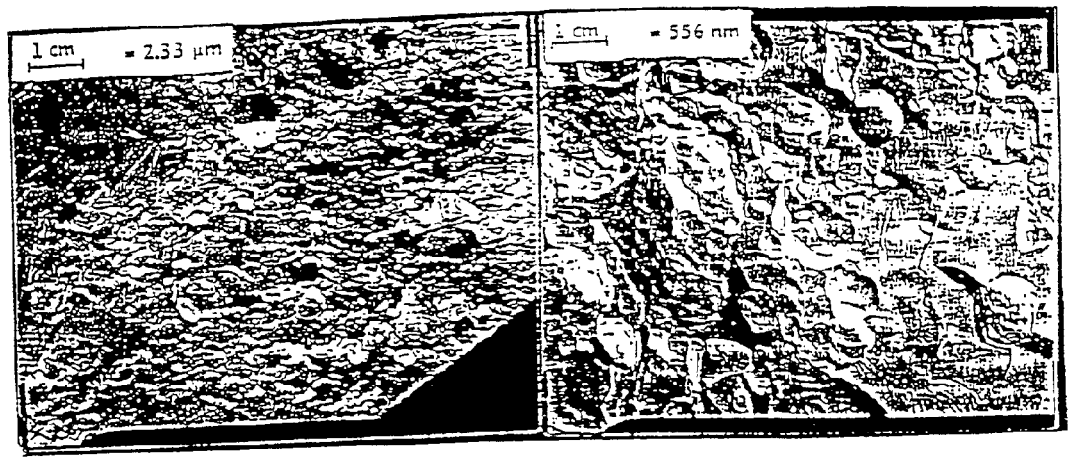
FIG. 5A is a Freeze Fracture photographic image showing cyclosporin A contained in negatively charged liposomes at 4,300× magnification.
FIG. 5B is a Freeze Fracture photographic image showing cyclosporin A contained in negatively charged liposomes at 18,000× magnification.

FIGS. 5A and 5B, prepared using the Freeze Fracture technique, are photographic images of negatively charged liposomes (as shown in, and described with respect to FIGS. 1A and 1B) at 4,300× and 18,000× magnification, respectively, containing cyclosporin A. After cyclosporin A was entrapped in the negatively charged liposomes as set forth above with respect to FIG. 3, the cyclosporin A/liposome combination was mixed with HA. Freeze Fracture images of the composition were then taken. The images show that multilamellar vesicle (MLV) liposomes were most prominent. That is, encapsulating cyclosporin A in the liposomes and then mixing the liposome/cyclosporin A composition with HA, did not alter the structure of the liposomal vesicles.

Figure 6:
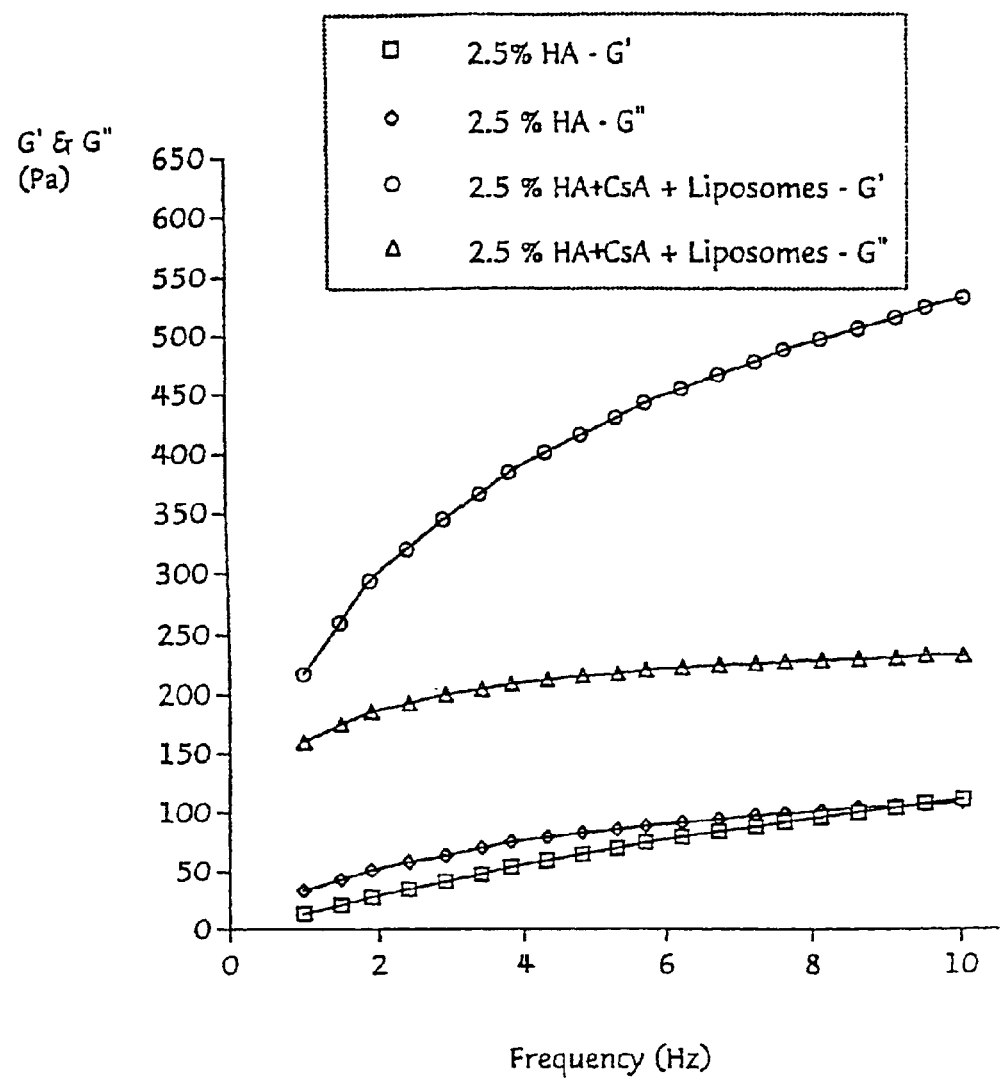
FIG. 6 is a graph showing an indicator of elasticity as measured by the storage modulus (G') and an indicator of viscosity as measured by the loss modulus (G") for HA, with and without negatively charged liposomes containing cyclosporin A versus frequency.

FIG. 6 is a graph showing the storage modulus (G') and loss modulus (G") for hyaluronic acid (product No. HG4003; molecular weight 630,000 daltons), with and without negatively charged liposomes (prepared using a Conventional Film technique) containing cyclosporin A, versus frequency. Cyclosporin A was encapsulated within the liposomes at a loading of 13.5 milligrams CsA per gram liposome as discussed above. Pure, dry HA powder was then mixed with the liposomelcyclosporin A composition (also as discussed above) such that the concentrations of the liposomes and HA were 13.165% by weight and 2.5% by weight, respectively. By plotting G' and G" versus frequency and noting the frequency at which G' and G" cross each other, the viscoelastic nature of the HA/liposome/cyclosporin A composition was determined as discussed above.

A difference in rheology between the two batches of HA (product Nos. HG4003 and HG4001) was observed. As shown in FIG. 6, the viscoelasticity for the HG4003 hyaluronic acid was much less than that for the HG4001 hyaluronic acid as indicated by the frequency at which G' (open squares) and G" (open diamond) cross one another. In particular, for the HG4003 hyaluronic acid alone, the cross-over frequency was about 10 hertz as shown in FIG. 6, compared to a cross-over frequency of about 5 hertz for the HG4001 hyaluronic acid as shown in FIG. 3. The reason for the difference in viscoelastic properties for the two hyaluronic acids may be due to impurities in the HG4003 HA sample.

Viscoelastic properties of HA were not adversely affected by mixing the liposome/cyclosporin A composition with HA. In fact, the storage modulus (G'; open circle) and the loss modulus (G"; open triangle) for liposome/cyclosporin A composition in HA were significantly higher than the storage modulus (G'; open square) and loss modulus (G"; open diamond) for HA alone as shown in FIG. 6. The cross-over frequency (the frequency at which G' and G" cross) for the liposomelcyclosporin A combination in HA is less than 1 hertz, while the cross-over frequency for HA alone is about 10 hertz indicating that the HA/liposome/cyclosporin A compositions are significantly more viscoelastic than HA alone. See FIG. 6. One explanation for the increased storage modulus (G') and loss modulus (G") is that the liposomes increase the strength and stability of HA gel composition.

Next, it was shown that negatively charged, positively charged, and neutral liposomes could be used in combination with HA according to the present invention. The liposomes used in the liposome/HA gel compositions shown in, and described with respect to FIGS. 7 and 8 were prepared using a Conventional Film technique. Negatively charged, positively charged and neutral liposomes suspended in HEPES buffer (having a pH of 7.4, 0.05 M) were mixed with sodium hyaluronic acid (product No. HG4003) as discussed above. The liposome/HA gel compositions were prepared such that the total lipid concentration, as measured in moles, remained constant. The HEPES buffer was filtered and degassed to remove oxygen and to minimize oxidation, thereby reducing the degradation of the unsaturated lipids. The control HA gel composition was 2.5% by weight HA in HEPES buffer.

Figure 7:
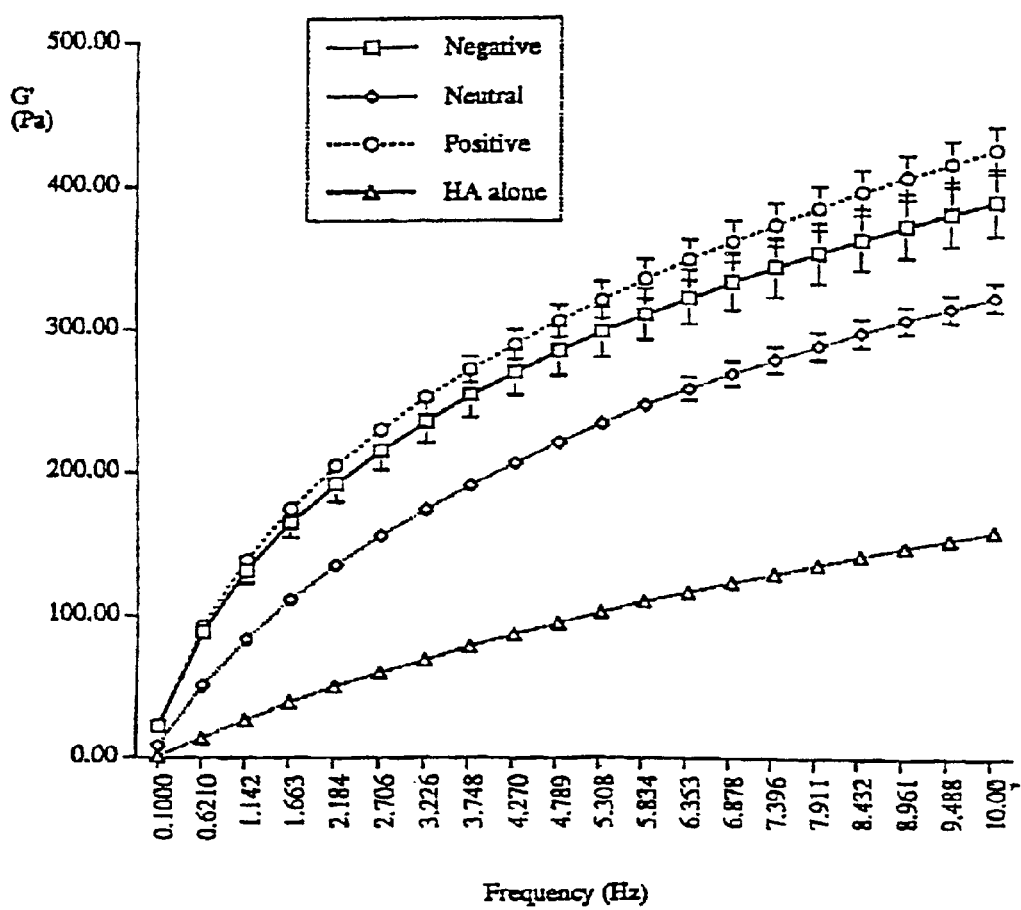
FIG. 7 is a graph showing an indicator of elasticity as measured by the storage modulus (G') versus frequency for negatively charged, positively charged, and neutral liposomes suspended in hyaluronic acid, and hyaluronic acid alone at time equals zero hours.
Figure 8:
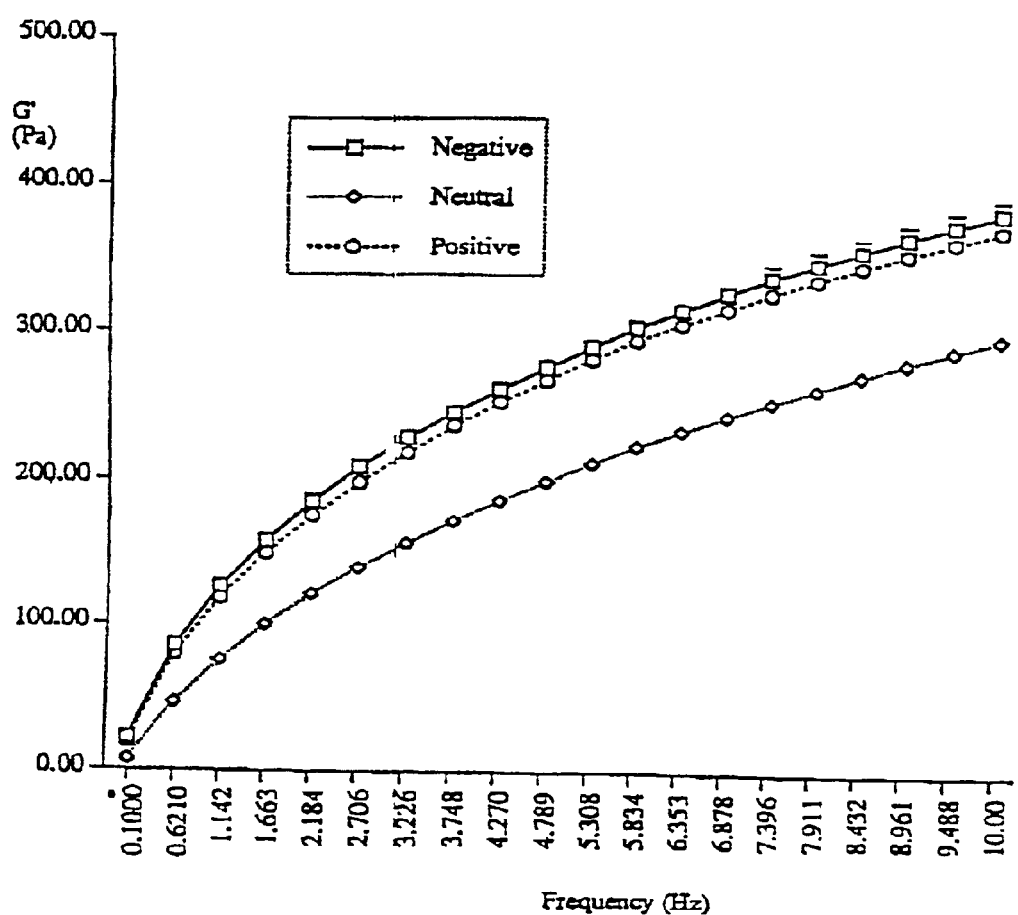
FIG. 8 is a graph showing an indicator of elasticity as measured by the storage modulus (G') versus frequency for negatively charged, positively charged, and neutral liposomes suspended in hyaluronic acid after 72 hours.

FIGS. 7 and 8 are graphs showing the elasticity as measured by the storage modulus (G') versus frequency for negatively charged, positively charged, and neutral liposomes in HA, and HA alone, versus frequency. FIG. 7 shows the storage modulus (G') versus frequency for such liposome/HA compositions initially, and FIG. 8 shows the storage modulus (G') for such liposome/HA compositions after 72 hours. The compositions shown in FIGS. 7 and 8 were fully hydrated. For each liposome/HA composition, the storage modulus (G') was 100–200% higher than the storage modulus (G') for HA alone. As indicated in FIG. 7 and Table 1, the positively charged liposomes in HA (open circle) had the highest storage modulus (G') values, followed by negatively charged liposomes (open square), and neutral liposomes (open diamond) in HA. All three liposome/HA compositions had storage moduli which were significantly higher than the storage modulus for HA alone (open triangle).

TABLE 1

Effect of Polarity and Presence of Liposomes on Storage Modules (G') of HA

| positively charged liposomes G' > in HA | negatively charged liposomes G' > in HA | neutral liposomes alone G'>> in HA | HA alone G' |
|---|---|---|---|

As shown in FIG. 8 and Table 2, after 72 hours similar results were found except that the storage modulus (G') for negatively charged liposomes (open square) in HA were about the same as the storage modulus for positive liposomes (open circle) in HA. Storage modulus (G') for neutral liposomes (open diamond) in HA again were less than the storage modulus (G') for the negatively and positively charged liposomes in HA. After 72 hours, the level of storage moduli (G') were as follows:

TABLE 2

Effect of Polarity and Presence of Liposomes on Storage Modules (G') of HA After 72 Hours

| positively charged liposomes G' ≈ in HA | negatively charged liposomes G' > in HA | neutral liposomes G' >> in HA | HA alone G' |
|---|---|---|---|

It was also shown that negatively charged, positively charged, and neutral liposomes did not adversely affect the viscoelastic properties of 2.5% by weight HA (product No. HG4003) gel compositions in the absence of any medicinal agent. The negatively charged, positively charged, and neutral liposomes and HA compositions were subjected to dynamic oscillatory testing and the Theological profiles were compared to those obtained for a control gel composition of 2.5% by weight HA in HEPES buffer.

Table 3 shows the mean storage modulus (G') for positively charged, negatively charged, and neutral liposomes in HA, and HA alone. As indicated above, the greater the reduction in mean storage modulus (G'), the less stable the gel. The storage moduli (G') were observed at frequencies of 5–10 Hz over a 72 hour period. After 72 hours, the change in mean storage modulus (G') for the positively charge liposomes (change in mean G'=−13.0%) and neutral liposomes (change in G'=−8.9%) in HA were greater than the change in the mean storage modulus (G') for negatively charged liposomes (change in mean G'=−2.3%) in 2.5% by weight HA, and for HA alone (change in mean G'=−1%). These results indicate that the positively charged and neutral liposomes in HA were less stable than negatively charged liposomes in HA, and HA alone. The smaller change in the mean storage modulus (G') for negatively charged liposomes in HA may account for the storage modulus (G') for negatively charged liposomes being higher than the storage modulus (G') for positively charged liposomes after 72 hours as shown in FIG. 8.

TABLE 3

(Six Samples Per Data Point)

| Liposomes in HA | mean G' at t = 0 | mean G' at t = 72 | % change in mean G' |
|---|---|---|---|
| Positive | 377 | 328 | −13.0 |
| Negative | 346 | 338 | −2.3 |
| Neutral | 281 | 256 | −8.9 |
| HA alone | 129 | 128 | −1.0 |

Table 4 shows the cross-over frequencies for positively charged, negatively charged, and neutral liposomes mixed with HA, and HA alone, initially and after 72 hours. As noted above, the lower the cross-over frequency of a substance, the more viscoelastic the substance. Cross-over frequency values for positively charged, negatively charged, and neutral liposomes and HA mixture were significantly less than cross-over frequencies for HA alone. This result supports the hypothesis that the presence of liposomes increased the strength and stability of HA gel compositions. Negatively charged liposomes in HA, however, exhibited the lowest cross-over frequency of all liposomes examined.

TABLE 4

(Six Samples Per Data Point)

| Liposomes in HA | Cross-over frequency (Hz) t = 0 | Cross-over frequency (Hz) t = 72 h |
|---|---|---|
| Positive | 1.3 | 1.2 |
| Negative | 1 | 1 |
| Neutral | 2.7 | 2.6 |
| HA alone | 7 | 7 |

Generally, it would appear that negatively charged and positively charged liposomes in HA increase the strength and stability of the HA gel composition more than neutral liposomes. However, all types of liposomes increase the elasticity of HA as compared to HA alone. The stability of the HA gel composition mixed with positively charged and neutral liposomes increased slightly, however, after 72 hours as indicated by the lower cross-over frequencies, whereas the stability of negatively charged liposomes mixed with HA, and HA alone did not increase. Table 4 shows that the cross-over frequencies of negatively charged, positively charged, and neutral liposomes in HA were significantly lower than the cross-over frequencies of HA alone, initially and after 72 hours. These results show that negatively charged, positively charged, and neutral liposomes in HA gel compositions were significantly more viscoelastic, and thus, more stable than HA gel compositions alone.

Antioxidant Activity of Hyaluronan (HA)

Liposomes are comprised of phospholipids which are readily oxidized. This oxidation process results in the reduction of the shelf life of liposomal preparations. It is believed that HA may decrease the rate of oxidation of phospholipids, because HA has also been reported to scavenge free radicals (Presti, D. & Scott, J. E., Cell Biochem. Function, 12, 281–288 (1994)). The oxidation process includes an initial conjugation of double bonds, and then cyclic-peroxides and hydroperoxides may form. These peroxides may then breakdown further into aldehydes and fatty acids.

No single assay will enable the absolute quantification of the oxidation of phospholipids, however, the measurement of the level of cyclic-peroxides within the formulation will give an indication as to the oxidative state of the phospholipids. This assay may be used to enable comparison between the efficacy of various antioxidants. The formation of the phospholipid oxidation product, cyclic-peroxide, within the CYCLOPS formulation (liposomes and HA), over a period of 28 days, was compared to the amount found in liposomes alone or liposomes containing the antioxidant α-tocopheryl acetate. The results of these comparative tests are displayed in FIG. 9.

Liposomes containing egg phosphatidylcholine were prepared by rotary evaporation and hydrated with HEPES buffer (pH 7.4). The liposome formulation included either no antioxidant or α-tocopheryl acetate, at 1% w/w of total lipid, or HA at 2.5% w/w of total formulation. The formation of the lipid oxidation product, cyclic peroxide, was investigated by heating samples of the formulation at 100° C. for 15 minutes in the presence of thiobarbituric acid. The assay was performed one day after the liposomes were prepared and over a period of 28 days, and the formulations were stored under nitrogen at 4° C.

Figure 9:
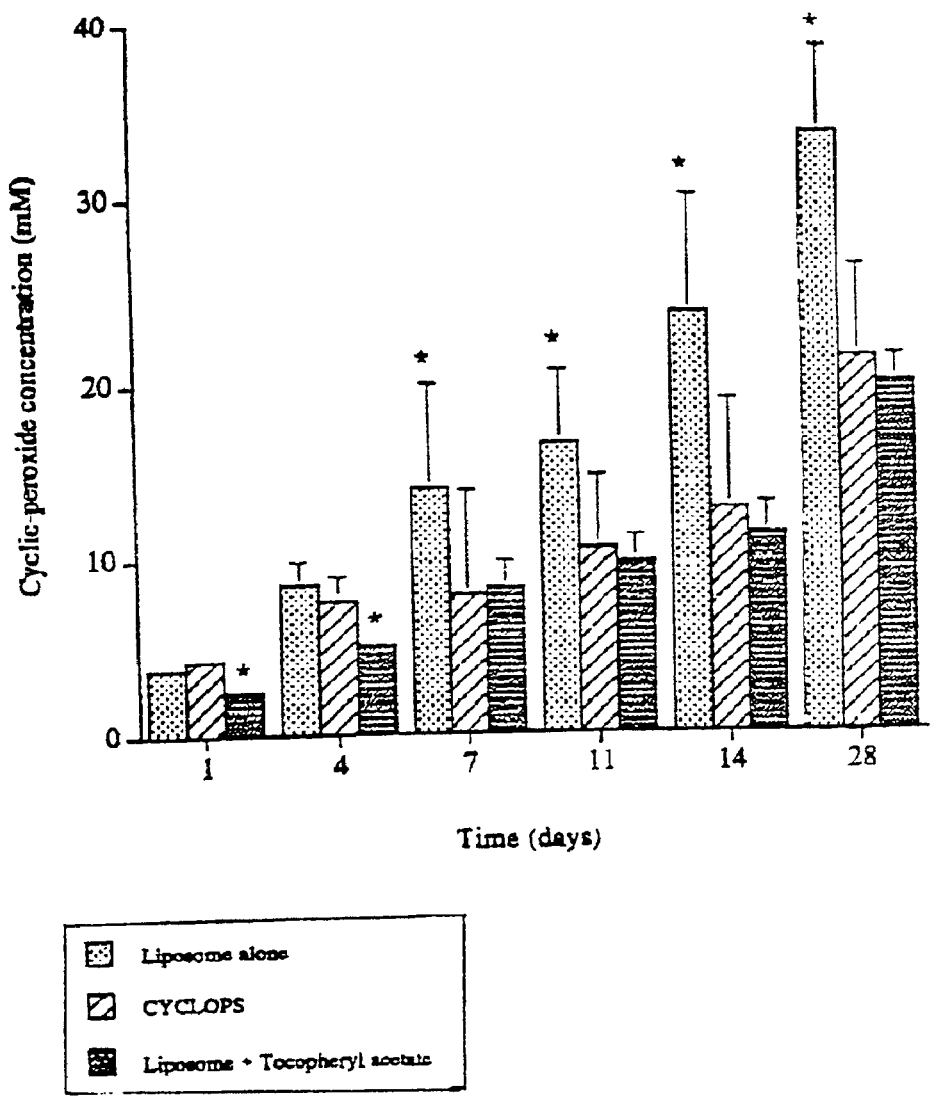
FIG. 9 is a graph showing comparative oxidation of formulations containing liposomes alone, liposomes with HA, and liposomes with α-tocopheryl acetate.

These experiments showed that after one day, liposomes formulated with α-tocopheryl acetate contained significantly less cyclic-peroxide than the CYCLOPS formulation and the liposomes formulation containing no antioxidant (FIG. 9). Nevertheless, when assayed after 7 days, the amount of cyclic peroxide within CYCLOPS and liposomes containing α-tocopheryl acetate was significantly reduced compared to liposomes alone. After 7, 11, 14, and 28 days, there was no significant observable difference between the amount of cyclic-peroxides within the formulation containing α-tocopheryl acetate and the CYCLOPS formulation.

HA significantly ($p<0.05$) decreased the amount of cyclic peroxide formed compared to liposomes comprising no HA or known antioxidant. The antioxidant activity of HA was not statistically different ($p>0.05$) from the unknown antioxidant, α-tocopheryl acetate.

The Cryopreservant Properties of HA

A method for extending the shelf life of liposomal formulations may be to remove the water from the formulation by lyophilization. Cryopreservants, such as the polysaccharide, trehalose, may be included in the formulation to protect the liposomes from damage during the lyophilization process. It is believed that HA may function as a cryopreservant and will enhance the stability of lyophilized liposomes.

Liposomes were prepared by the conventional film method and were used to hydrate HA to give a 2.5% w/w gel. Freeze fracture electron micrographs of the formulation were taken using a transmission electron microscope (EM301G, Philips electron optics, Cambridge, UK) before lyophilization. A sample of the formulation was then lyophilized overnight and then stored under nitrogen at 4° C. for one week. The sample was then rehydrated with the required amount of water and then freeze fracture electron micrographs were taken. Additionally, thin layer chromatography (TLC) of the rehydrated formulation was performed. A 500 mg sample of the formulation was dried under argon and was reconstituted in 100 μL of a 2:1 v/v/ chloroform:methanol solution, to obtain a concentration of 55 mg mL$^{-1}$ of phospholipid. A 10 μL aliquot was spotted onto a TLC plate and aliquots (10 μL) of lysophosphatidylcholine (LPC) standards were included. The plate was run with a mobile phase of 65:35:2.5:2.5 v/v chloroform:methanol:ammonium hydroxide:water and was then sprayed with 50:50 v/v solution of Molybdenum blue spray (Sigma, Dorset, UK): 4.2 M sulfuric acid to visualize the lipids.

Figure 10:
FIG. 10 is a Freeze Fracture photographic image showing cyclosporin A contained in liposomes and HA before lyophilization at 8,650× magnification.
Figure 11:
FIG. 11 is a Freeze Fracture photographic image showing cyclosporin A contained in liposomes and HA before lyophilization at 14,400× magnification.
Figure 12:
FIG. 12 is a Freeze Fracture photographic image showing cyclosporin A contained in liposomes and HA after lyophilization at 15,350× magnification.
Figure 13:
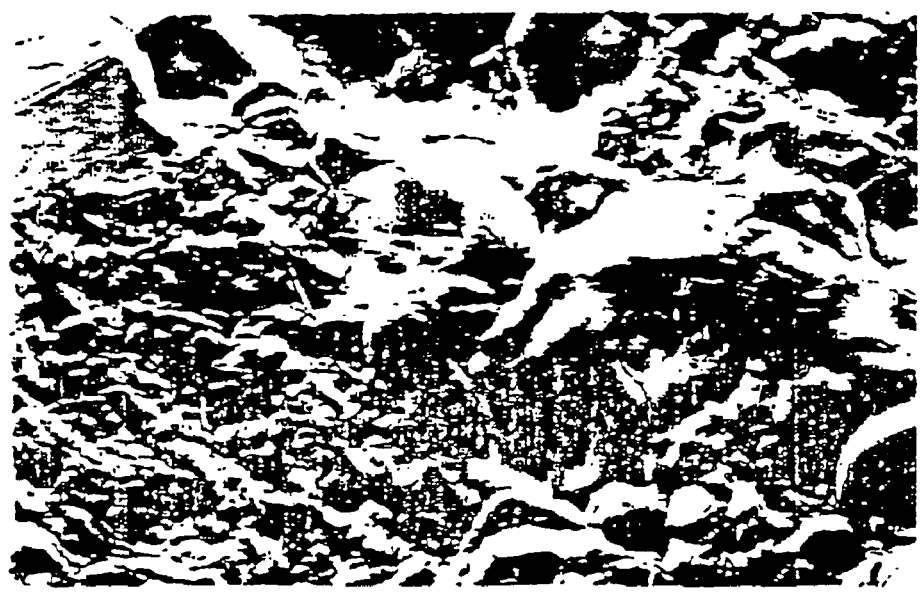
FIG. 13 is a Freeze Fracture photographic image showing cyclosporin A contained in liposomes and HA after lyophilization at 9,230× magnification.

The electron micrographs, depicted in FIGS. 10 & 11, taken at 8,650× magnification and 14,400× magnification, respectively, show that liposomes were present within the formulation before lyophilization. Electron micrographs of the rehydrated formulation, depicted in FIGS. 12 & 13, taken at 15,350× magnification and 9,230× magnification, respectively, show that liposomes were still present after undergoing the lyophilization process and a week of storage as lyophilized powder. LPC is a product of the spontaneous hydrolysis of phosphatidylcholine and may be used as a measure of the integrity of the phospholipid. No spots corresponding to LPC were observed using on the electron micrographs TLC when the formulation was examined before and after lyophilization (limit of LPC detection is 0.05 mg mL$^{-1}$).

HA within the formulation is believed to act as a cryopreservant, because liposomes were readily formed when the CYCLOPS formulation was rehydrated after one week of storage as a powder. During the lyophilization process, less than 0.1% of the phospholipids were hydrolyzed into LPC. Nevertheless, the effects of HA on the long term stability of the lyophilized formulation may only be determined by examination over a longer period of time.

Deposition of Cyclosporin A in the Skin

Previously, clinical trials of topical cyclosporin formulations were not therapeutically successful (Bousema et al., J. Am. Acad. Dermatol., 22, 126–27 Brief Communication (1990)). Nevertheless, the formulation of drugs within liposomes has been shown to increase the deposition of drugs within the epidermis (Egbaria et al., Skin Pharmacol., 4, 21–28 (1991)). Additionally, HA has been shown to enhance drug deposition in the skin, for example, increased amounts of diclofenac were found in the skin when HA was included in its formulation (Brown et al., Int. J. Tissue React., XVII, 133–140 (1995)). Therefore, the combination of both liposomes and HA is believed to enhance the amount of cyclosporin A found within the skin.

Excised human skin was mounted in Franz cells and 250 μL of either liposomes or the CYCLOPS formulation containing radioactive cyclosporin A was applied to the surface of the skin. After an incubation period of 48 hours, the formulation was washed from the skin and the plug of CYCLOPS formulation that had formed on the skin surface was removed using Scotch Magic Tape (810, 3M). The epidermis and dermis were then separated by containing the skin section within a plastic sachet and the immersing it in water at 70° C. for 60 seconds. After being separated, the epidermis and dermis were solubilized in soluene overnight and an aliquot was removed and added to a scintillation cocktail (Ultima Gold, Beckman). The radioactive counts were calculated as a percentage of the counts applied.

Figure 14:
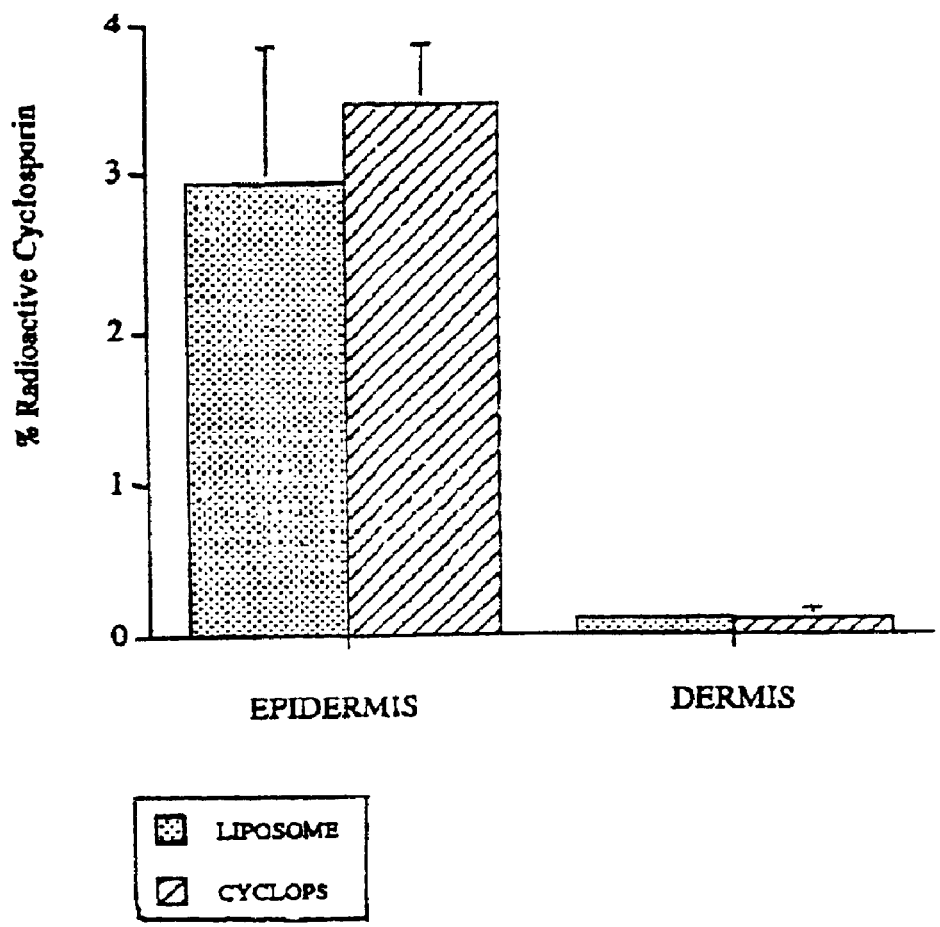
FIG. 14 is a graph showing the comparative radioactive presence of cyclosporin A in the epidermis and dermis of the skin in formulations containing HA and liposomes and liposomes only.

Both the liposomes and CYCLOPS formulation resulted in a deposit of cyclosporin A within the epidermis at approximately 3% of the total radioactivity applied to the surface of the skin. These results are shown in FIG. 14 in which the comparative percentage radioactivities of the CYCLOPS formulation (with 2.5% w/w hyaluronan) and the liposome formulation (without hyaluronan) in the epidermis and dermis of the skin after 48 hours is depicted. An increased amount of cyclosporin A was deposited within the skin when applied, in the CYCLOPS formulation than in the liposome formulation alone, however, this increase was not significant (p>0.05) for the number of skin sections examined (n=3). The amount of cyclosporin A in the dermis was small and no cyclosporin A was detected in the receiver chamber of the Franz cell.

The percentage of cyclosporin A within the epidermis was at a level that would have a therapeutic effect in the treatment of the disease, psoriasis. Thus, the CYCLOPS formulation is believed to have potential as a novel topical formulation of cyclosporin A.

The above examples and experiments also indicate that cyclosporin A can be successfully mixed with HA gel compositions by first encapsulating cyclosporin A in liposomes, and then mixing the liposome/cyclosporin A composition with HA. The results also indicate that the presence of liposomes within HA does not affect the viscoelastic nature of HA. Indeed, the results indicate that liposomes increase the viscoelasticity of HA gels. One possible explanation is that liposomes increase the inter- and intra-chain hydrophobic bonding of the HA gel compositions. Hyaluronic acid also stabilizes and protects liposomes from breakdown, thus overcoming one of the major problems associated with delivery of drugs in liposomes. Thus, the HA/liposome compositions according to the present invention are ideally suited for the topical and non-topical delivery of drugs in general, and are not limited to the encapsulation and delivery of CsA, although it appears that this system is particularly efficacious for encapsulation and delivery of hydrophobic drugs not ordinarily compatible with HA.

Hyaluronic acid/liposome pharmaceutical compositions containing therapeutically effective amounts of drugs such as cyclosporin A according to the present invention may be safely and efficaciously topically administered to animals. For example, a pharmaceutical composition having 2.5% by weight hyaluronic acid, 13.2% by weight liposomes having 13.5 milligram cyclosporin A per gram liposome encapsulated therein, may be topically applied to a surface of an internal or external organ or tissue, including the skin of an animal in a therapeutically effective amount to treat any condition at or near that surface for which non-systemically delivered CsA is pharmacologically effective.

HA/liposome pharmaceutical compositions containing therapeutically effective amounts of drugs are not limited to topical applications, however. Rather they may be administered to animals, including humans orally, parenterally or intrarectally in dosage amounts determined essentially entirely by the effective dosage of the pharmaceutical component with which the liposome/HA carrier system is combined, since the carrier system itself is non-toxic. The amount of liposome/HA carrier used may be easily determined by those skilled in the art, using other targeted vehicle systems as a model.

While various specific embodiments of the present invention have been described, modifications and substitutions may be made by those skilled in the art without departing from the true spirit and scope of the present invention. Accordingly, any modified or substituted variants of the present invention should be understood to fall within the scope of the appended claims inasmuch as the invention has been described by way of illustration only and not limitation.

What is claimed is:

1. A dermal pharmaceutical composition comprising hyaluronic acid, multilamellar liposomes, and cyclosporin A, wherein said cyclosporin A is encapsulated in said liposomes, wherein said liposomes and said hyaluronic acid are mixed in proportions sufficient to form a viscoelastic gel being more viscoelastic than said hyaluronic acid alone, and having a dermal permeability exceeding that of the hyaluronic acid alone, wherein said pharmaceutical composition contains 13.165% by weight liposomes, 2.5% hyaluronic acid by weight of the composition, and 13.5 milligrams cyclosporin A per gram liposomes.

2. A method for preparing a dermal pharmaceutical composition comprising hyaluronic acid, multilamellar liposomes, and cyclosporin A, wherein said cyclosporin A is encapsulated in said liposomes, wherein said liposomes and said hyaluronic acid are mixed in proportions sufficient to form a viscoelastic gel being more viscoelastic than said hyaluronic acid alone, and having a dermal permeability exceeding that of the hyaluronic acid alone, wherein said pharmaceutical composition contains 13.2% by weight liposomes, 2.5% by weight hyaluronic acid, and 13.5 milligrams cyclosporin A per gram liposomes, said method comprising:

(i) producing said liposomes from phospholipids in the presence of said cyclosporin A;
(ii) encapsulating said cyclosporin A in said liposomes; and
(iii) mixing said liposomes with said hyaluronic acid to form a viscoelastic gel that is more viscoelastic than said hyaluronic acid alone.

3. A dermal pharmaceutical composition comprising hyaluronic acid, multilamellar liposomes, and cyclosporin A, wherein said cyclosporin A is encapsulated in said liposomes, wherein said liposomes and said hyaluronic acid are mixed in proportions sufficient to form a viscoelastic gel being more viscoelastic than said hyaluronic acid alone, and having a dermal permeability exceeding that of the hyaluronic acid alone, wherein said pharmaceutical composition contains 13.165% by weight liposomes, 2.5% by weight hyaluronic acid, and 1.32% by weight cyclosporin A.

4. A pharmaceutical composition comprising hyaluronic acid, multilamellar liposomes, and cyclosporin A, wherein said cyclosporin A is encapsulated in said liposomes, wherein said liposomes and said hyaluronic acid are mixed in proportions sufficient to form a viscoelastic gel being more viscoelastic than said hyaluronic acid alone, and wherein phospholipids used to prepare the liposomes aer selected from the group consisting of phosphatidyl serine, phosphatidyl glycerol, and combinations thereof, wherein said pharmaceutical composition contains 13.165% by weight liposomes, 2.5% by weight hyaluronic acid, and 1.32% by weight cyclosporin A.

* * * * *

UNITED STATES PATENT AND TRADEMARK OFFICE
CERTIFICATE OF CORRECTION

PATENT NO. : 6,890,901 B2
DATED : May 10, 2005
INVENTOR(S) : Christopher Marriott et al.

It is certified that error appears in the above-identified patent and that said Letters Patent is hereby corrected as shown below:

<u>Title page,</u>
Item [56], References Cited, OTHER PUBLICATIONS, insert
-- R.R.C. New, "Liposomes - A Practical Approach", Oxford University Press, pp. 1-32, (1990).

J.E. Scott, "Hyaluronan, Multum in Parvo", European Journal of Rheumatology & Inflammation, Vol. 15, Issue 1, pp. 3-8, (1995).

Martin, "Phospholipids as Skin Penetration Enhancers", King's College, University of London, London, United Kingdom, pp. 57-84, (1993).

Gregoriadis, "Liposomes in Drug Delivery: Present and Future", In: Liposome Dermatics, Eds. O. Braun-Falco, H.C. Horting and H.I. Maibach, Springer, Heidelberg, pp. 346-352, (1992). --.

Signed and Sealed this

Twenty-fifth Day of April, 2006

JON W. DUDAS
*Director of the United States Patent and Trademark Office*